United States Patent [19]
Brown et al.

[11] Patent Number: 5,368,576
[45] Date of Patent: Nov. 29, 1994

[54] NEEDLE SAFETY DEVICE

[76] Inventors: Melissa Brown; Mike Brown, both of 2111 Michie Dr., Apt. 111, Charlottesville, Va. 22901; Ajay Jagtiani, 6126 Rocky Way Ct., Centreville, Va. 22020

[21] Appl. No.: 891,971

[22] Filed: May 26, 1992

[51] Int. Cl.⁵ .............................................. A61M 5/32
[52] U.S. Cl. ................... 604/192; 206/210; 206/364; 206/365; 206/366
[58] Field of Search ............... 604/110, 192, 263, 406, 604/414; 206/364–367, 210, 205, 459.1, 523, 370, 524

[56] References Cited

U.S. PATENT DOCUMENTS

| | | | |
|---|---|---|---|
| 3,899,295 | 8/1975 | Halpern | 422/56 |
| 3,944,069 | 3/1976 | Eldridge, Jr. | |
| 4,758,229 | 7/1988 | Doerschner | |
| 4,792,053 | 12/1988 | Towns et al. | 215/250 |
| 4,845,923 | 7/1989 | Donovan | 53/431 |
| 4,927,415 | 5/1990 | Brodsky | |
| 4,979,945 | 12/1990 | Wade et al. | 604/192 |
| 4,981,476 | 1/1991 | Aichlmayr et al. | |
| 4,989,307 | 2/1991 | Sharpe et al. | |
| 5,038,929 | 8/1991 | Kubofcik | 206/210 |
| 5,234,732 | 8/1993 | Versic et al. | 428/35.7 |

Primary Examiner—C. Fred Rosenbaum
Assistant Examiner—V. Alexander
Attorney, Agent, or Firm—Fisher & Associates

[57] ABSTRACT

A needle safety device is provided which allows a health care professional to dispose of a needle quickly and safely while also only using only one hand. The safety device comprises a housing having an orifice therethrough; a puncture detection system in the housing and comprising a first membrane secured over the orifice, a pH sensitive dye, and a gas for raising the pH above normal atmospheric conditions; and a securing system in the housing and comprising a curable adhesive, a curing agent, and a membrane for temporally separating said adhesive from said curing agent.

18 Claims, 1 Drawing Sheet

NEEDLE SAFETY DEVICE

FIELD OF THE INVENTION

This invention relates generally to the disposal of needles and more specifically, to a device for safe disposal of needles by preventing further contact of a needle tip with the outside environment.

BACKGROUND OF THE INVENTION

Needle safety has long been a concern of health care professionals. The recent spread of infections diseases such as Acquired Immune Deficiency Syndrome (AIDS) has changed a needle prick from a minor irritation to a potentially fatal injury.

Medical needles generally are covered by a protective cap when not in use. When the needle is so covered, it presents little to no possibility of a health care professional being pricked by the needle. A danger is created from the instant that the needle is removed from its protective cap.

Current medical practice calls for the removal of all needles from a patient during an emergency. These needles are removed from the patent and are often threaded through a bedsheet or disposed of in devices described below. By threading a needle into a bedsheet, a health care professional may be accidentally pricked while caring for the patient. Occasionally, these needles are forgotten and end up pricking someone responsible for the care and maintenance of the linens.

In an attempt to reduce the potential for needle pricks, several devices have been created. These devices fall into two general categories, needle disposal devices and needle guards.

U.S. Pat. No. 4,989,307, Sharpe et al., discloses a needle disposal device. This device comprises an orifice for accepting needle tips, a rotational device for removing the needle tips, and a bag for accepting the unattached needle tips. This device requires that a health care professional place the needle tip into a small orifice and that a switch be manipulated to remove the needle tip from the rest of the assembly. In an emergency, it is rarely possible to have the time necessary to place the needle carefully into the small orifice. Thus, a needle prick may occur while trying to dispose of the needle within a small orifice.

U.S. Pat. No. 3,944,069, Eldridge, and 4,758,229, Doerschner, disclose needle disposal devices comprising a pair of foldable pads. The pads have a penetration resistant outer coatings which when folded over the needle prevents further contact with the needle. These devices require that a health care professional remove a needle and place it horizontally upon the pad. Then the professional would fold the pad over so as to cover the needle. Thus, two hands must be used to dispose of the needle. This exposes the health care professional to the needle tip several times.

U.S. Pat. No. 4,981,476, Aichlmayr et al. discloses a needle guard which comprises a cap which is spring biased to close when the needle is extracted from a patient. This needle guard has the disadvantage of being difficult to use when initially inserting the needle into the patient. By having to pull back the guard upon inserting the needle into the patient, a health care professional's hand is exposed to the needle area. This increases the likelihood of an accidental needle prick.

U.S. Pat. No. 4,927,415, Brodsky, discloses a needle guard which comprises a needle, a hollow tube surrounding a part of the needle, a pulling member attached to the needle and passing through the hollow tube, and a closable end on the hollow tube. The device operates by a health care professional pulling upon the pulling member. This in turn causes the needle to withdraw past the closable end of the hollow tube and be secured within the hollow tube. This device requires that a health care professional use two hands to dispose of a needle. The first hand is used to grasp the hollow tube and the second hand grasps the pulling member. In addition, the needle is left dangling while it is being pulled into the hollow tube.

U.S. Pat. No. 4,979,945, Wade et al., discloses a needle cap resheather comprising a plurality of needle caps, a clamp for holding the caps, and a means for mounting the clamp to a bed. In operation, a health care professional would reinsert a needle into one of the caps that is suspended in the clamp. This presents the problem of inserting a needle into a very small orifice and generally increases the likelihood of a needle prick.

Although all of the above-discussed devices relate to needle safety, they have various disadvantages of requiring a health care professional to insert the needle into a small orifice, reducing the useability of the needle, causing additional exposure to the needle when disposing of the needle, or requiring the health care professional to use two hands in the disposal process.

SUMMARY OF THE INVENTION

According to the invention, a needle safety device is provided which has the advantage allowing a health care professional to dispose of a needle quickly and safely while also only using one hand.

According to a preferred embodiment of the invention, the safety device comprises a housing having an orifice therethrough, a puncture detection means secured to the orifice for detecting the presence of a needle, and a securing means for maintaining the needle in the housing. Additionally, a mounting means may be provided to secure the housing to a conventional bed rail or iv post.

Other features and advantages of the invention will be set forth in, or apparent from, the following detailed description of the preferred embodiment of the invention.

DESCRIPTION OF THE PREFERRED EMBODIMENTS

Figure 1:
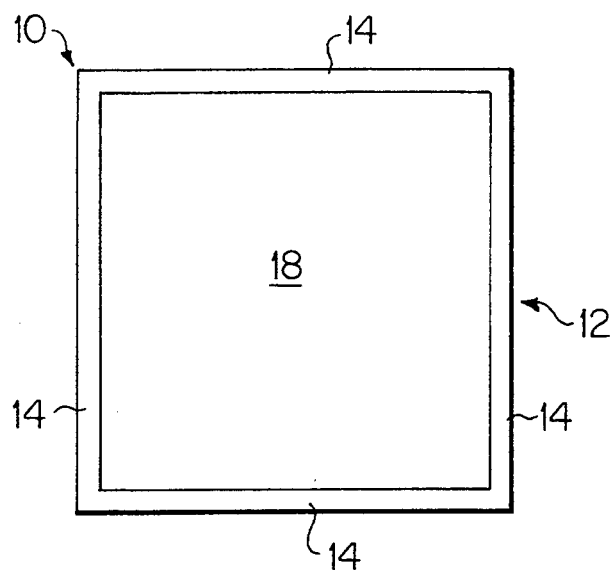
FIG. 1 is a front elevational view of a needle safety device constructed in accordance with a preferred embodiment of the invention.
Figure 2:
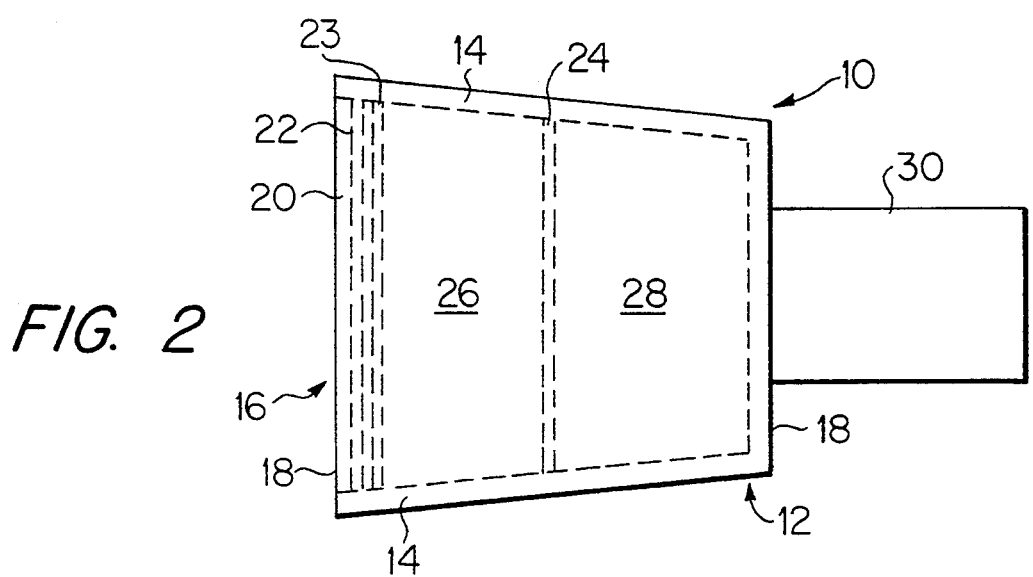
FIG. 2 is a side elevational view of the device of FIG. 1.
Figure 3:
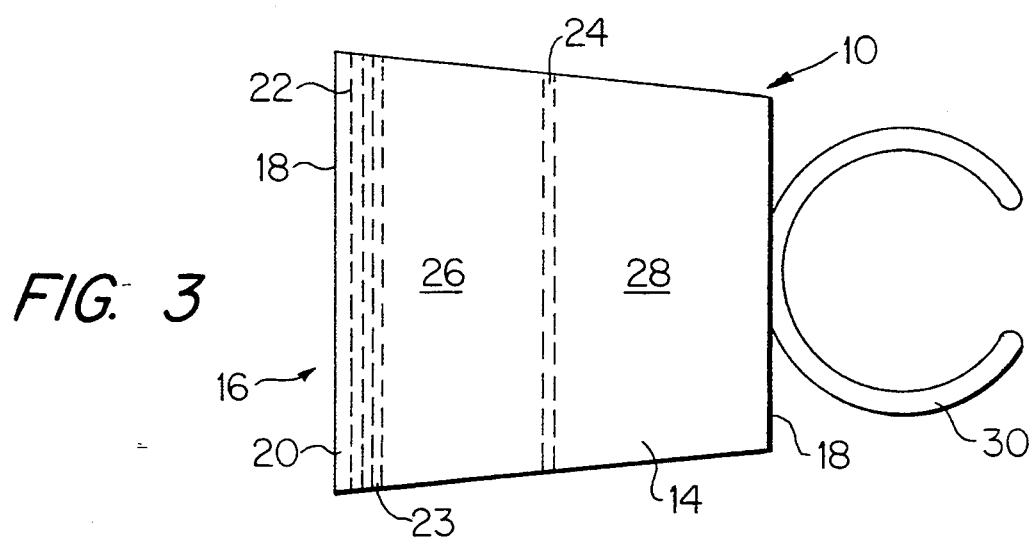
FIG. 3 is a plan view of the device of FIG. 1.

Referring to FIG. 1, 2 and 3, a needle safety device, generally denoted 10, is shown. The safety device 10 comprises a housing 12 which in a preferred embodiment will be made from a plastic sheet material having at least a ⅛" thickness or any other material which will prevent the penetration of a needle. The housing 12 will have four solid sides 14 which are preferably in the shape of a trapezoid and are orientated so that, when attached, the housing has a front and rear face 16 and 18, respectively. Rear face 18 is covered by the plastic material and front face 16 is left open to form an orifice.

It should be noted that the front face 16 is larger than the rear face 18. This size differential is important in that it will allow a greater surface area on face 16, while allowing the remainder of the safety device 10 to be relatively small, and thus make it easier for a health care professional to place a needle in the safety device 10, through the orifice formed by face 16. It should be noted that the housing 12 may be of any shape which can be defined by a quadric. These shapes include, but are not limited to, conicoids, spheres, spheroids, eillpsoids, paraboloids, hyperboloids, or a cone or cylinder with a circular base.

A membrane 20 is secured over face 16 and to sides 14 to provide an airtight compartment between sides 14 and faces 16 and 18. Membrane 20 is designed to be easily punchurable by a needle. In a preferred embodiment, the membrane 20 will be translucent to allow for the layers beneath to be seen. Disposed below membrane 20 is a detection layer 22.

Detection layer 22 will vary with the particular item to be detected. For example, detection layer 22 may be designed to be sensitive to the puncturing of membrane 20. In a preferred embodiment, this will be accomplished by providing a sheet which is coated with a dye which is one color at atmospheric pH and a second color at above normal atmospheric pH. Thus, in operation, the sheet may be white in above atmospheric pH and red at atmospheric pH. The pH level will be maintained above the atmospheric pH by providing a gas having a high pH, such as ammonia, in sufficient concentration to hold the dye white. Once a needle punctures the membrane 18, the gas will escape the housing and thus reduce the concentration of the gas in contact with the dye. This reduction in concentration will cause the pH level to approach that of the atmosphere and in turn cause the dye to change color. By releasing a gas such as ammonia into the atmosphere, the health care professional has two warning indicators of the presence of a needle in device 10. First, there is the visual color change of the dye. Second, there is the distinctive odor of ammonia in the atmosphere.

A second example of a detection layer 22 is to use a sheet with a dye which is oxidizable with an accompanying color change in the presence of oxygen. This system would be constructed by providing an oxygen sensitive layer which is maintained in vacuum or in an anaerobic condition by the membrane 20. In operation, the puncturing of membrane 20 will allow the vacuum to be filled with atmosphere. This exposure will cause a color change in the oxygen sensitive layer. The use of an oxygen sensitive layer has the advantage of being usable in environments, such as the intensive care unit, where the presence of ammonia will cause problems to the patient or equipment.

A third example of a detection layer that may be used is one in which develops a color change upon exposure to plasma, white blood cells, red blood cells, hemoglobin, antigens, antibodies or any other testable element of the blood.

Immediately disposed behind detection layer 22 is a first separator membrane 23. The separator membrane 23 is designed to prevent the gases, chemicals, or reacting agents from contact with other material below. Additionally, the membrane 23 is designed to be easily punctured by a needle. A second separator membrane 24 is disposed in the void between the first separator membrane 23 and the rear face 18 and thus forming two voids 26 and 28, respectively. Voids 26 and 28 are filled with a curable adhesive, such as epoxy, and a curing agent, such as a hardener, respectively. Any epoxy and hardener may be utilized which has the characteristics of being very fast acting and quickly setting.

Secured to the rear face 18 is a mounting device 30. In a preferred embodiment, the mounting device 30 will be formed of the same material as housing 12 and will have a C shape. The C shape allows for the mounting of the needle safety device 10 on conventional bed poles and IV stands.

Considering the overall operation of the needle safety device 10, a health care professional would place device 10 upon a bed pole or iv stand of a patient receiving an iv needle. In the event of an emergency, the needle would be removed from the patient, by the health care professional, and would have the pointed end of the needle placed through membranes 18, 22 and 24. Once a needle punctures the membrane 18, ammonia gas will escape the housing and thus reduce the concentration of the gas in contact with the dye. This reduction in concentration will cause the pH level to approach that of the atmosphere and in turn cause the dye to change color. Additionally, the puncturing of membrane 24 will cause the curable adhesive in void 26 to mix with the curing agent in void 28. A chemical reaction will take place between the curable adhesive and the curing agent to produce a hardened adhesive which will prevent the removal of the needle from the housing 12. This needle safety device 10 has the advantage of complying with OSHA regulations and allows the use of only one hand while in operation. Additionally, the device provides a visual and olfactory indication of the presence of the needle in the device.

Although the present invention has been described relative to specific exemplary embodiments thereof, it will be understood by those skilled in the art of medical safety equipment that variations and modifications can be effected in these exemplary embodiments without departing from the scope and spirit of the invention. For example, the detection layer may be modified to detect any desired substance such as other body fluids or presence/absence of solids, liquids, or gasses without departing from the spirit of the invention. Another example is the selection or modification of the curable adhesive and hardening agent.

What is claimed is:

1. A needle safety device for allowing a health care professional to quickly dispose of a needle with the use of only one hand, said device comprising:
   a housing having an orifice therethrough;
   a needle detection means secured to said orifice for detecting the presence of a needle; and
   a securing means disposed within said housing, said securing means for maintaining said needle in said housing, said securing means comprising a curable adhesive, a curing agent, and a membrane for temporally separating said adhesive from said curing agent.

2. The device recited in claim 1, wherein said housing has four sides, each having a trapezoidal shape, and a rear face opposite said orifice and attached to said four sides.

3. The device recited in claim 2 wherein each of said four sides are orientated so that said rear face has a smaller surface area than said orifice.

4. The device recited in claim 1 wherein said housing has a shape which may be defined as a quadric.

5. The device recited in claim 1 wherein said needle detection means includes an indicator oxidizable with an accompanying color change in the presence of a gas.

6. The device recited in claim 1 wherein said needle detection means develops a color upon exposure to hemoglobin.

7. The device recited in claim 1 wherein said needle detection means includes an indicator containing a pH sensitive dye.

8. The device recited in claim 1 further comprising an attaching means for securing said safety device to a bed pole.

9. The device recited in claim 8 wherein said attaching means comprises a C shaped clip, said clip secured to said housing.

10. A needle safety device for allowing a health care professional to quickly dispose of a needle with the use of only one hand, said device comprising:
a housing having an orifice therethrough;
a puncture detection means secured to said orifice for detecting the presence of a needle, said puncture detection means comprising a first membrane secured over said orifice, a pH sensitive dye, and a gas for raising the pH above normal atmospheric conditions; and
a securing means for maintaining said needle in said housing, said securing means comprising an adhesive.

11. The device recited in claim 10, wherein said housing has four sides, each having a trapezoidal shape, and a rear face opposite said orifice and attached to said four sides.

12. The device recited in claim 11 wherein each of said four sides are orientated so that said rear face has a smaller surface area than said orifice.

13. The device recited in claim 10 wherein said housing has a shape which may be defined as a quadric.

14. The device recited in claim 10 further comprising an attaching means for securing said safety device to a bed pole.

15. The device recited in claim 14 wherein said attaching means comprises a C shaped clip, said clip secured to said housing.

16. A needle safety device for allowing a health care professional to quickly dispose of a needle with the use of only one hand, said device comprising:
a housing having an orifice therethrough;
a puncture detecting means secured to said orifice for detecting the presence of a needle, said puncture detection means comprising an indicator having an accompanying color change which is initiated by the presence of a gas;
a securing means for maintaining said needle in said housing, said securing means comprising an adhesive; and
attaching means for securing said safety device to a bed pole.

17. The device recited in claim 16, wherein said housing has four sides, each having a trapezoidal shape, and a rear face, wherein each of said four sides are orientated so that said rear face, being opposite said orifice and attached to said four sides, has a smaller surface area than said orifice.

18. The device recited in claim 16 wherein said housing has a shape which may be defined as a quadric.

* * * * *